US00PP23952P2

(12) United States Plant Patent
Kordes

(10) Patent No.: US PP23,952 P2
(45) Date of Patent: Oct. 8, 2013

(54) MINATURE ROSE PLANT NAMED 'KORPOT005

(50) Latin Name: *Rosa hybrida*
Varietal Denomination: KORpot005

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 88 days.

(21) Appl. No.: 13/385,490

(22) Filed: Feb. 21, 2012

(51) Int. Cl.
*A01H 5/00* (2006.01)

(52) U.S. Cl.
USPC ..... Plt./118

(58) Field of Classification Search
USPC ..... Plt./118
See application file for complete search history.

(56) References Cited

U.S. PATENT DOCUMENTS

PP17,402 P2 * 2/2007 Kordes ..... Plt./118
PP19,460 P2 * 11/2008 White ..... Plt./118

OTHER PUBLICATIONS

Pluto QZ UPOV Citation for 'KORpot005' Feb. 22, 2011.*

* cited by examiner

*Primary Examiner* — Wendy C Haas

(57) ABSTRACT

A new and distinct variety of rose with long lasting, novel yellow flowers, and attractive foliage with very good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot005'. The new variety of rose plant of the present invention originated from a controlled crossing in a breeding program of two distinct parents during the summer of 2006. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot005'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. 'KORpot005' has very large, yellow flowers, whereas the seed parent has large, deep yellow flowers.
2. 'KORpot005' has good disease resistance, whereas the seed parent has low disease resistance.

The new rose plant may be distinguished from its pollen parent, an 'un-named seedling', by the following combination of characteristics:

1. 'KORpot005' has yellow flowers, whereas the pollen parent has cream yellow flowers.
2. 'KORpot005' flowers have an elegant shape, whereas the pollen parent flowers have a roundish shape.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot005' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot005' was selected in May, 2007 from the seedling beds to be asexually propagated for further evaluation. The first asexual propagation of 'KORpot005' was done by rooting softwood cuttings in June, 2007 at the inventor's nursery in Offenseth-Sparrieshoop, Germany.

This initial and other subsequent propagations conducted in controlled environments demonstrate that 'KORpot005' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORpot005'.

DETAILED BOTANICAL DESCRIPTION

The following is a description of 'KORpot005', as observed growing in February, 2012 in a nursery in Jackson County, Oreg. on plants 4 months of age. Color references are made using The Royal Horticultural Society (London, England) Colour Chart, 2001 except where common terms of color are used.

For a comparison, several physical characteristics of the rose variety 'KORfrosdra', a rose variety from the same inventor described and illustrated in U.S. Plant Pat. No. 20,208 and issued on Aug. 4, 2009 are compared to 'KORpot005' in Chart 1.

CHART 1

| Characteristic | 'KORpot005' | 'KORfrosdra' |
|---|---|---|
| Petal count | 55-70 | 25-30 |
| Sepal length | 15-20 mm | 20-27 mm |
| Stigma position | Slightly superior to anthers | Inferior to anthers |

Parents:

*Seed parent.*—'Un-named seedling'.

*Pollen parent.*—'Un-named seedling'.

Classification:

*Botanical classification.*—*Rosa hybrida* 'KORpot005'.

*Commercial classification.*—Miniature rose.

FLOWER AND FLOWER BUD

Blooming habit: Recurrent.

Flower bud:

*Size.*—Upon opening, 25 mm in length from base of receptacle to distal end of bud and 15 mm diameter at its widest point.

*Bud form.*—Short, globular.

*Bud color.*—As sepals first unfold, bud color is Yellow Group 12D. When ¼ open, the upper surface of petals is Yellow Group 12C, and the lower surface is Yellow Group 11D. Guard Petals have intonations of Yellow-Green Group 145B on petal margins and basal zone.

*Sepals.*—Color: Upper surface Yellow-Green Group 146D. Lower surface Yellow-Green Group 146C. Size: Average 15-20 mm (l)×7-9 mm (w). Shape: Moderately strong foliaceous appendages on three of the five sepals. Apex: Apiculate. Base: Flat at union with receptacle. Quantity: Five. Surface texture: Upper side: Pubescent. Lower surface: Lightly pubescent with occasional stipitate glands. Margins: Pubescent with stipitate glands.

Receptacle:

*Surface.*—Smooth.

*Color.*—Yellow-Green Group 144B.

*Shape.*—Urn-shaped.

*Size.*—10 mm (h)×15 mm (w).

Peduncle:

*Surface.*—With fine hairs and stipitate glands.

*Length.*—20 to 25 mm average length.

*Diameter.*—2 to 3 mm average diameter.

*Color.*—Yellow-Green Group 146C.

*Strength.*—Strong.

*Borne.*—Singularly.

Flower bloom:

*Fragrance.*—Light.

*Duration.*—On the plant 10 to 14 days. Long lasting. As a cut flower, 6 to 8 days. Senesced petals drop away cleanly.

*Size.*—Large for a miniature rose. When open, the average flower diameter is 60-80 mm and the average flower height is 25-30 mm.

*Form.*—Shape of flower when viewed from the side: Upon opening, upper part: Flat. Upon opening, lower part: Flattened convex. Open flower, upper part: Flat. Open flower, lower part: Flattened convex.

Color:

*Upon opening, petals.*—Outermost petals: Outer Side: Yellow-Orange Group 14B, with upper petal margin of Yellow-Orange Group 14D. Inner Side: Yellow-Orange Group 21C, with petal margin of Yellow-Orange Group 20B. Innermost petals: Outer Side: Orange Group 24C, with a petal base of Yellow-Orange Group 15B. Inner Side: Yellow-Orange Group 23B, with a petal base of Yellow-Orange Group 15C and overtones of Orange Group 28C.

*Upon opening, basal petal spots.*—No distinctive coloration at petal base observed.

*After opening, petals.*—Outermost petals: Outer Side: Yellow-Orange Group 19C, with basal margins of Yellow-Orange Group 14B. Inner Side: Yellow-Orange Group 14D, with a basal area of Yellow Group 13C. Innermost petals: Outer Side: Yellow-Orange Group 14C, with overtones of Yellow-Orange Group 19C in the marginal zone. Inner Side: Yellow Group 15C.

*After opening, basal petal spots.*—No distinctive coloration at petal base observed.

General tonality: On open flower, Yellow-Orange Group 16C. No change in the general tonality at the end of the 5$^{th}$ day. Afterwards, general tonality is Yellow-Orange Group 16D.

Petals:

*Petal count.*—Very double.

*Average range.*—Approximately 55-70 petals under normal conditions.

*Petal reflex.*—Petals reflex slightly.

*Petal edge.*—Entire, with small point in center of margin.

*Petal shape.*—Broadly ovate. Apex shape is round with a small point in the center. Shape of base is attenuate.

*Petal size.*—30-35 mm (l)×15-30 mm (w).

*Thickness.*—Average.

*Petal arrangement.*—Not formal.

Petaloids:

*Petaloid count.*—Average of 4-8 per flower.

*Petaloid size.*—Petaloids are 10-15 mm (l) and 5-10 mm (w).

*Petaloid color.*—Color of inner side is Yellow-Orange Group 16A. Color of outer side is Yellow-Orange Group 16C.

*Petaloid texture.*—Thick.

*Margins.*—Strongly reflexed, indented, highly irregular.

*Petaloid shape.*—Most commonly deltoid, with some petaloids highly irregular. Apex: Ovoid. Base: Acute.

Reproductive organs:

*Pistils.*—Few. Approximately 20 present. Stigmas: Location: Slightly superior in position to anthers. Color: Yellow Group 3B. Styles: Length: About 4 mm long. Color: Yellow-Green Group 145C.

*Stamens.*—Approximately 30 on average and regularly arranged. Anthers: Size: Average 5 mm long. Pollen: Generally present. Color: Greyed-Orange Group 165A. Filaments: Color: Yellow-Orange Group 14B. Length: 8 mm.

THE PLANT

Growth: Moderately vigorous.

Plant habit: Compact, upright to bushy habit. When grown as a 15 cm pot plant, the average plant height is 20-25 cm and the average plant width is 17 cm.

Blooming: Floriferous, repeat blooming.

Stems:

*Stem color.*—Young wood: Yellow-Green Group 144B. Older wood: Yellow-Green Group 144A.

*Stem surface.*—Young wood: Smooth. Older wood: Smooth.

Prickles: Present.

*Incidence.*—Average of 2-4 per each 10 cm of stem.

*Size.*—Average length: 3-4 mm.

*Color.*—Immature prickles: Greyed-Red Group 182B. Mature prickles: Greyed-Orange Group 176B.

*Shape.*—Linear.

Leaves and leaflets: Normally 5 leaflets on normal leaves in middle of the stem.

*Venation pattern.*—Pyramidal net pattern.

*Leaf size.*—80-85 mm (l)×50-60 mm (w).

*Abundance.*—Average.

*Texture.*—Thin. Upper side of leaflet: Semi-glossy. Under side of leaflet: Matte.

*Color, mature foliage.*—Upper Leaf Surface: Green Group 137A. Lower Leaf Surface: Green Group 137C.

*Color, juvenile foliage.*—Upper Leaf Surface: Green Group 137B. Lower Leaf Surface: Yellow-Green Group 146B. Anthocyanin intonation: Present. Intonations present on immature leaflet edge and lower side, Greyed-Orange Group 176C.

Stipules:

*Size.*—7 mm long, 3 mm from distal tip to distal tip.

*Stipule color.*—Yellow-Green Group 146A.

*Stipitate glands.*—Present on margins.

*Margins.*—Cirrose.

*Shape.*—Apex: Apiculate. Base: Slightly winged.

Petiole:

*Length.*—Average 12-15 mm.

*Diameter.*—Average 1-1.5 mm.

*Petiole color.*—Yellow-Green Group 146A.

*Underneath.*—Small prickles and stipitate glands.

*Margins.*—With stipitate glands.

*Anthocyanin.*—Greyed-Orange Group 17C on lower side.

Petiole rachis:

*Length.*—Average 15-18 mm.

*Diameter.*—Average 1 mm.

*Color.*—Yellow-Green Group 176B.

*Margins.*—With stipitate glands.

Leaflets:

*Size.*—Average size of the terminal leaflet is 35-40 mm (l)×18-22 mm (w).

*Shape.*—Ovate. Base: Broadly obtuse. Apex: Acute.

*Margins.*—Finely serrated.

*Surface.*—Upper: Semi-glossy. Lower: Matte.

*Texture.*—Thin.

*Arrangement.*—Odd pinnate.

*Venation.*—Reticulate.

Hips/seed formation: None observed.

Winter hardiness: Unknown.

Disease resistance: Very good resistance to Powdery mildew (*Sphaerotheca pannosa*), and *Botrytis* (*Botrytis cinerea*) diseases under normal greenhouse growing conditions.

I claim:

1. A new and distinct variety of rose plant, as described and illustrated herein.

* * * * *

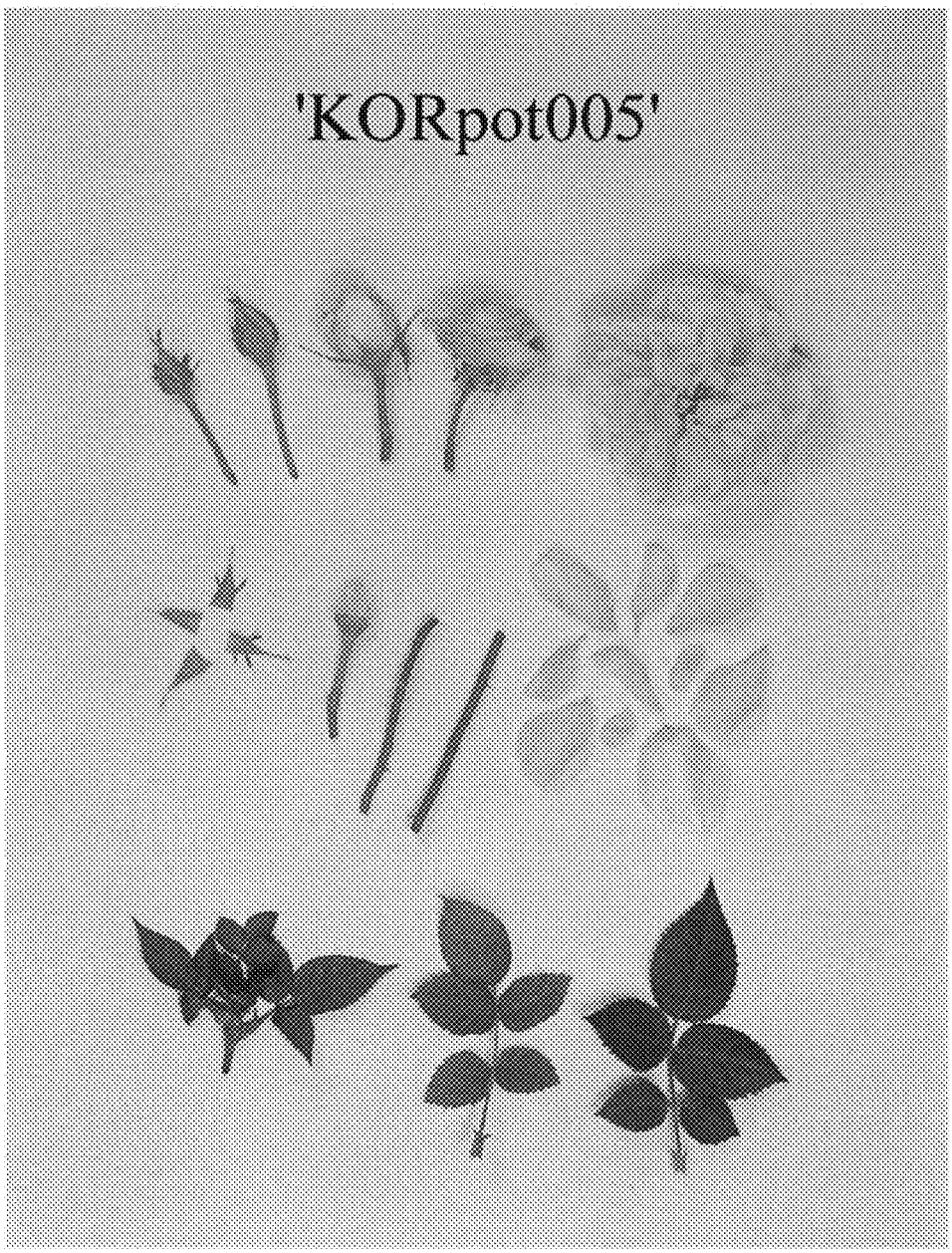
'KORpot005'